United States Patent [19]

Bottanet et al.

[11] Patent Number: 5,041,626

[45] Date of Patent: Aug. 20, 1991

[54] INTERMEDIATE COMPOUNDS USABLE FOR THE PREPARATION OF HERBICIDES

[75] Inventors: Bernard Bottanet, Vienne; Michel Mulhauser, Ecully, both of France

[73] Assignee: Rhone-Poulenc Agrochimie, Lyons, France

[21] Appl. No.: 363,297

[22] Filed: Jun. 7, 1989

Related U.S. Application Data

[63] Continuation of Ser. No. 156,180, Feb. 16, 1988, abandoned.

[30] Foreign Application Priority Data

Feb. 19, 1987 [FR] France .................... 87 02435

[51] Int. Cl.$^5$ .................................. C07F 9/38
[52] U.S. Cl. ................................ 562/15; 71/87
[58] Field of Search ........................ 562/15, 16, 17

[56] References Cited

U.S. PATENT DOCUMENTS 3,927,080 12/1975 Gaertner ..................... 260/502.5
4,422,982 12/1983 Subramanian ................. 260/502.5
4,675,429 6/1987 Borrod et al. ................ 558/145
4,755,614 7/1988 Corbet ........................ 558/134

FOREIGN PATENT DOCUMENTS 2144425 3/1985 United Kingdom .

Primary Examiner—J. E. Evans
Attorney, Agent, or Firm—Morgan & Finnegan

[57] ABSTRACT

The invention relates to compounds of formula:

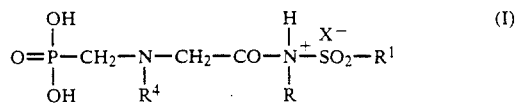

in which $R^4$ is a group which can be hydrogenolyzed, R and $R^1$ are alkyl groups, $X^-$ is an $HSO_4^-$, $Cl^-$ or $R^7SO_3^-$ anion and to a process for the preparation of the compounds of formula (I) by the hydrolysis of the compounds of formula (II):

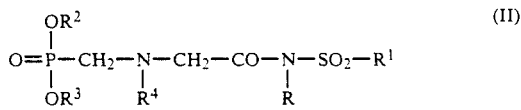

in which $R^2$ and $R^3$ are alkyl groups linked to the oxygen via a secondary carbon, using sulphuric or hydrochloric acid. The invention also relates to the use of compounds of formula (I) for the preparation of herbicide by the hydrogenolysis of the compounds of formula (I).

10 Claims, No Drawings

INTERMEDIATE COMPOUNDS USABLE FOR THE PREPARATION OF HERBICIDES

This is a continuation of co-pending application Ser. No. 07/156,180, filed on Feb. 16, 1988, now abandoned.

DESCRIPTION OF THE INVENTION

The invention relates to new compounds, to the process for the preparation thereof and to the use thereof as intermediates for the preparation of compounds of formula:

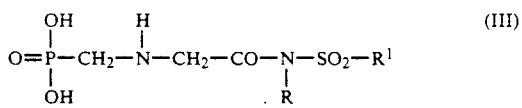

in which:

$R^1$ represents a hydrocarbon radical, preferably alkyl, aryl or cycloalkyl, including substituted radicals wherein the substituents are for example, halogen atoms and phenyl, cyano, alkyl, alkoxy or alkyl carboxylate groups, in which the alkyl groups preferably contain from 1 to 4 carbon atoms; $R^1$ perferably containing from 1 to 18 carbon atoms, preferably from 1 to 7 carbon atoms and more preferably from 3 to 7 carbon atoms when it is a cycloalkyl group; $R^1$ preferably being an optionally halogenated, preferably chlorinated or fluorinated, alkyl radical containing from 1 to 4 carbon atoms, e.g., $CF_3$; and in which R represents a hydrogen atom or has one of the meanings given for $R^1$, and is preferably an alkyl group containing from 1 to 4 carbon atoms. Related processes are described in EP-A-0,135,454.

One of the objects of the Present invention is to provide an improved industrial Process for making compounds of formula (III).

Another object is to prepare compounds suitable as intermediates for the preparation of compounds of formula (III).

Another object of the present invention is to provide a simplified process of implementation.

Another object of the present invention is to provide a process which is ecologically advantageous.

Compounds of the invention are of formula:

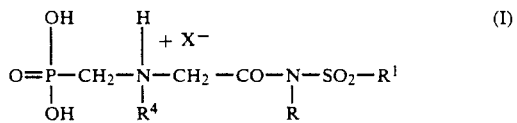

in which R and $R^1$ have the same meaning as in the compound of formula III described above, $X^-$ is an $HSO_4^-$, $Cl^-$ or $R^7SO_3^-$ anion;

$R^4$ represents a hydrogen atom or a group which can be hydrogenolyzed; Preferably a radical of formula $Ar(R^5)(R^6)C-$ in which Ar is an aromatic group, preferably phenyl, and $R^5$ and $R^6$ are hydrogen atoms or an Ar radical or an alkyl group preferably containing not more than 6 carbon atoms, $R^7$ represents an optionally mono- or polyhalogenated $C_1$ to $C_4$ alkyl group, preferably trifluoromethyl. R and $R^1$ preferably correspond to methyl group. $X^-$ is preferably an $HSO_4^-$ anion.

The invention also relates to a process for the preparation of compounds of formula (I), wherein an acid chosen from amongst $H_2SO_4$, HCl or $HSO_3R^7$, or a mixture thereof is reacted with a compound of formula:

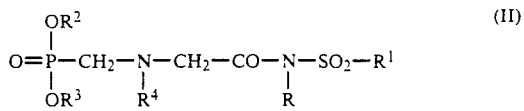

in which $R^1$, R and $R^4$ have the same meaning as in the compound of formula (I), and $R^2$ and $R^3$, which may be identical or different, are optionally substituted alkyl or aralkyl groups generally containing from 3 to 12 carbon atoms and preferably from 3 to 8 carbon atoms in the case of the alkyl groups and 8 to 12 carbon atoms in the case of the aralkyl groups, preferably 8 carbon atoms, said groups being linked to the oxygen atom via a secondary carbon atom, and $R^7$ represents an optionally mono- or Polyhalogenated $C_1$ to $C_4$ alkyl group, preferably trifluoromethyl.

PREPARATION OF FORMULA (I)

The reaction is carried out by heating (II) in the presence of an acid. The temperature is generally between 50° C. and 100° C., preferably between 60° C. and 90° C. If the reaction is carried out in the presence of a solvent, the preferred solvent is a polar solvent, e.g. water, $C_1$ to $C_6$ aliphatic carboxylic acids such as acetic acid, and $C_1$ to $C_3$ aliphatic alcohols such as methanol. Among these solvents, $C_1$ to $C_6$ aliphatic carboxylic acids, alone or in the form of a mixture, are preferred.

Sulphuric acid is also preferred because it leads to excellent yields and because it also leads to an easy separation of the resulting salt and to ecologically acceptable byproducts.

The normality of the acid will preferably be between 2N and pure. Advantageously, a normality for the sulphuric acid preferably between 10 and 30N will be employed.

Preferably, at least two equivalents of $H^+$ ions per mole of compound of formula II are employed. Between 2 and 10 equivalents, and preferably between 2.5 and 4 equivalents of $H^+$ ions per mole of compound II are employed.

The process is more particularly suitable for compounds in which R and $R^1$ are alkyl groups. $R^2$ and $R^3$, which may be identical or different, preferably correspond to isopropyl, isobutyl, isopentyl or cyclohexyl groups. Preferably, $R^2$ and $R^3$ correspond to isopropyl groups.

PREPARATION OF FORMULA (III)

The reaction of compounds of formula (I) to produce compounds of formula (III) is characterized by the hydrogenolysis of the compound of formula (I), in the presence of a catalyst, in a solvent which is capable of dissolving the compound of formula:

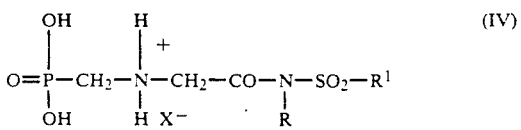

in which R, $R^1$ and X have the same meaning as in the compound of formula (III), followed by the addition of an acceptor for acid. Thus, another advantage of the invention is that it enables a hydrogenolysis of the group $R^4$ to be carried out without intermediate separation. Most commonly, this is a debenzylation. The reaction is advantageously carried out in an aqueous or alcoholic medium at ambient temperature or above, and at atmospheric Pressure or above. Catalysts suitable are those which are usually employed for the hydrogenolysis of the radicals $R^4$ under consideration. Such catalysts include palladium, platinum and Raney nickel. The catalyst may be employed with or without an inert support. These metals, especially palladium and platinum, may be employed in the form of salts, hydroxides or oxides, which are converted into the corresponding metal under the influence of hydrogen. Palladium-based catalysts such as palladium on charcoal or palladium on barium sulphate or palladium hydroxide on charcoal are employed as the preferred debenzylation catalyst. When the reaction is complete, the catalyst may be separated by filtration.

The solvent is preferably a polar solvent, e.g., water, $C_1$ to $C_6$ carboxylic acids and $C_1$ to $C_3$ alcohols. Of the carboxylic acids, acetic acid is preferred. Of the alcohols, methanol is preferred.

The compound of formula (III) is recovered by adding an acceptor for acid in at least a stoichiometric quantity. Suitable acid acceptors include organic or inorganic bases, preferably sodium or potassium hydroxides or carbonates, as well as amines of which the salt with an acid is soluble in the solvent chosen, such as tris(alkyl) amines, preferably triethylamine, tripropylamine, tributylamine and N,N-dialkylaniline.

EXAMPLES

The following examples, given without implied limitation, are illustrative of the invention.

EXAMPLE 1

A Product having the following formula (17.36 g; $4 \times 10^{-2}$ moles);

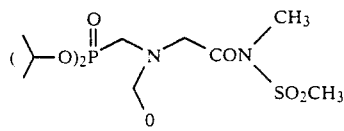

and 25N sulphuric acid (9 2 cc; $11.48 \times 10^{-2}$ mole) are heated for 4 h at 75° C. The mixture is cooled to 40° C. Methanol (40 cc and palladinized charcoal (0.48 g) containing 5% by weight of palladium are added to the above solution. The mixture is then placed under a hydrogen atmosphere. When the theoretical quantity of hydrogen is absorbed, the mixture is filtered and the residue washed with methanol (70 cc). A solution of triethylamine (11.6 g; $11.48 \times 10^{-2}$ mole) in methanol (40 cc) is added, in the course of 1 h, into the reaction mixture maintained at 20° C. When the addition is complete, a precipitate appears. The latter is filtered after 15 min. The solid, after being placed in an oven heated to 70° C. at 25 torrs, has a mass of 7.81 g and the content of product of formula

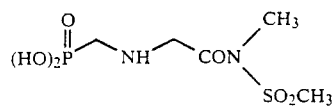

thereof is greater than 99% (determination by HPLC), which corresponds to a yield of the isolated Product of 75%.

EXAMPLE 2

The product of the following formula (17.36 g; $4 \times 10^{-2}$ mole):

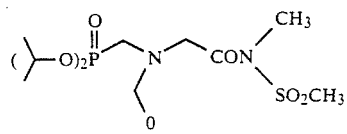

and a 20N solution (17.3 cc) of sulphuric acid in acetic acid are heated for 4 hours at 60° C. The mixture is cooled and then treated as in Example 1 (17.36 g of triethylamine are employed for the precipitation). The solid obtained has a mass of 9.05 g, which corresponds to a yield of the isolated product of 87%.

EXAMPLE 3

The product of the following formula (17.36 g; $4 \times 10^{-2}$ mole): and a 37% solution (34.72 g) of hydrochloric acid in water are heated for 4 h at 60° C. in a closed flask. The mixture is cooled. Pd/C containing 5% by weight of palladium (0.7 g) and methanol (40 cc) are added. The mixture is stirred under a hydrogen atmopshere at 40° C. As soon as hydrogen absorption is complete, the catalyst is filtered off and the mixture is concentrated under vacuum at 40° C. The residue is diluted with methanol (200 cc) and water (50 cc). Triethylamine (4.75 g), as determined after chloride determination, in methanol (10 cc) is added at 20° C.

After filtering and drying, 7.6 g of the product are isolated, which corresponds to a yield of 73%.

EXAMPLE 4

The reaction is carried out as in Example 1, using tributylamine (21.23 g) instead of triethylamine. The yield of the isolated Product is 81%.

What is claimed is:

1. A process for the preparation of the compounds of the formula:

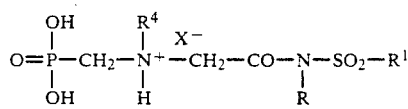

in which $R^1$ represents a hydrocarbon radical,

R represents a hydrogen atom or a hydrocarbon radical, $R^4$ represents a group which can be hydrogenolyzed; and $X^1$ is an $HSO^-_4$, $Cl^-$ or $R^7SO^-_3$ anion where $R^7$ is an optionally mono- or polyhalogenated $C_1$ to $C_4$ alkyl group.

wherein a compound of formula:

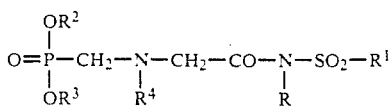

(II)

in which $R^1$, R and $R^4$ have the same meaning as in formula (I) and $R^2$ and $R^3$, which may be identical or different, are optionally substituted alkyl or aralkyl groups containing from 3 to 12 carbon atoms when said group is an alkyl group and 8 to 12 carbon atoms when said group is an aralkyl group, said groups are linked to the oxygen atom via a secondary carbon, is reacted in the presence of an acid selected from the group consisting of hydrochloric acid, sulphuric acid or sulphonic acids $R^7SO_3H$, where $R^7$ is an optionally mono- or polyhalogenated $C_1$ to $C_4$ alkyl group.

2. A process according to claim 1 wherein $R^2$ and $R^3$ contain from 3 to 8 carbon atoms when said group is a substituted alkyl group and 8 carbon atoms when said group is a substituted aralkyl group.

3. The process according to claim 1, wherein the reaction is carried out in a polar organic solvent selected from the group consisting of $C_1$ to $C_6$ aliphatic carboxylic acids, a mixture of two or more of said acids, and $C_1$ to $C_3$ alcohols.

4. The process according to claim 1, wherein the normality of the acid is between 2N and the maximum normality attainable for the acid in aqueous solution and wherein between about 2.5 and about 4 equivalents of $H^+$ ions per mole of compound of formula II are employed.

5. A process of claim 1 wherein the reaction temperature is between 40° C. and 100° C.

6. A process of claim 1 wherein the acid is sulphuric acid.

7. A process of claim 3 wherein the acid is sulphuric acid.

8. A process of claim 1 wherein R and $R^1$ are methyl groups.

9. A process of claim 1 wherein $R^2$ and $R^3$, which may be identical or different, are isopropyl, isobutyl, or isopentyl groups.

10. A process of claim 8 wherein $R^2$ and $R^3$ are isopropyl.

* * * * *